United States Patent
Martin

(10) Patent No.: US 8,516,795 B2
(45) Date of Patent: Aug. 27, 2013

(54) EXHAUST GAS SENSOR DEVICE, ENGINE CONTROL DEVICE AND METHOD

(75) Inventor: Alexander Martin, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 327 days.

(21) Appl. No.: 12/796,146

(22) Filed: Jun. 8, 2010

(65) Prior Publication Data

US 2011/0000192 A1 Jan. 6, 2011

(30) Foreign Application Priority Data

Jul. 1, 2009 (DE) .......................... 10 2009 027 374

(51) Int. Cl.
*F01N 11/00* (2006.01)

(52) U.S. Cl.
USPC ................ 60/276; 60/274; 60/285; 73/23.31; 73/23.32

(58) Field of Classification Search
USPC ............... 60/274, 276, 285; 73/23.31, 23.32, 73/31.01, 31.05
See application file for complete search history.

(56) References Cited

U.S. PATENT DOCUMENTS

| | | | | |
|---|---|---|---|---|
| 4,109,615 A | * | 8/1978 | Asano | 123/686 |
| 4,198,851 A | * | 4/1980 | Janata | 73/31.06 |
| 4,271,798 A | * | 6/1981 | Seitz et al. | 123/436 |
| 4,391,256 A | * | 7/1983 | Sawada et al. | 60/276 |
| 5,698,771 A | | 12/1997 | Shields et al. | |
| 6,238,536 B1 | | 5/2001 | Lundgren et al. | |
| 6,286,493 B1 | * | 9/2001 | Aoki | 123/690 |
| 6,450,007 B1 | * | 9/2002 | O'Connor | 73/23.2 |
| 7,036,982 B2 | * | 5/2006 | Smith et al. | 374/144 |
| 2007/0220954 A1 | * | 9/2007 | Fleischer et al. | 73/31.05 |
| 2008/0016949 A1 | * | 1/2008 | Fleischer et al. | 73/31.06 |
| 2009/0056313 A1 | | 3/2009 | Kama et al. | |

FOREIGN PATENT DOCUMENTS

EP 1 845 369 10/2007

* cited by examiner

*Primary Examiner* — Thomas E. Denion
*Assistant Examiner* — Jorge Leon, Jr.
(74) *Attorney, Agent, or Firm* — Kenyon & Kenyon LLP

(57) ABSTRACT

An exhaust gas sensor device for detecting a concentration of at least one exhaust gas component in the exhaust gas line of an internal combustion engine is described, having at least one ChemFET for detecting the oxygen content of the exhaust gas. In addition, a corresponding engine control device and an engine control method are described.

17 Claims, 4 Drawing Sheets

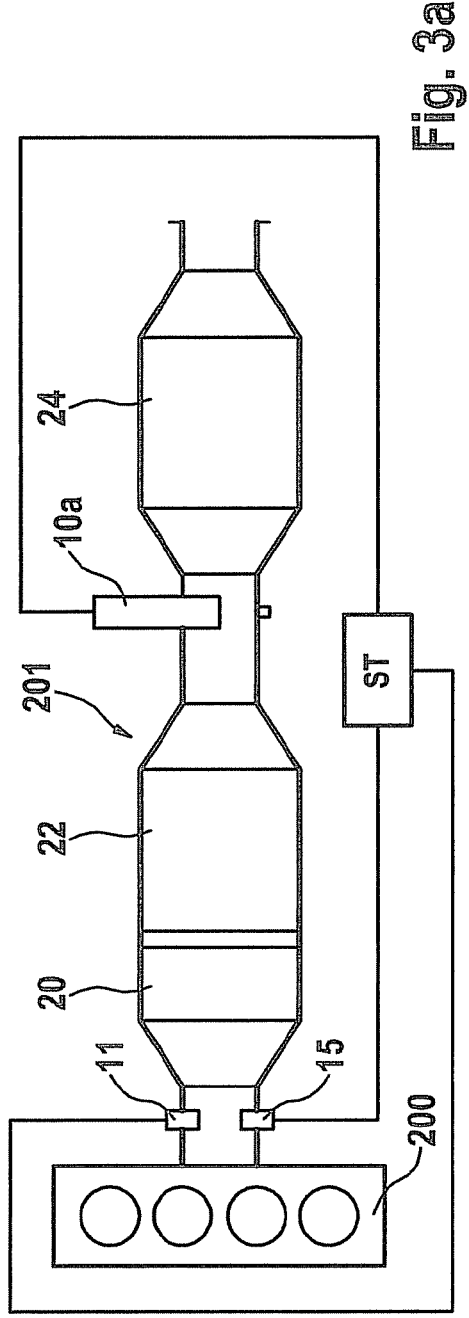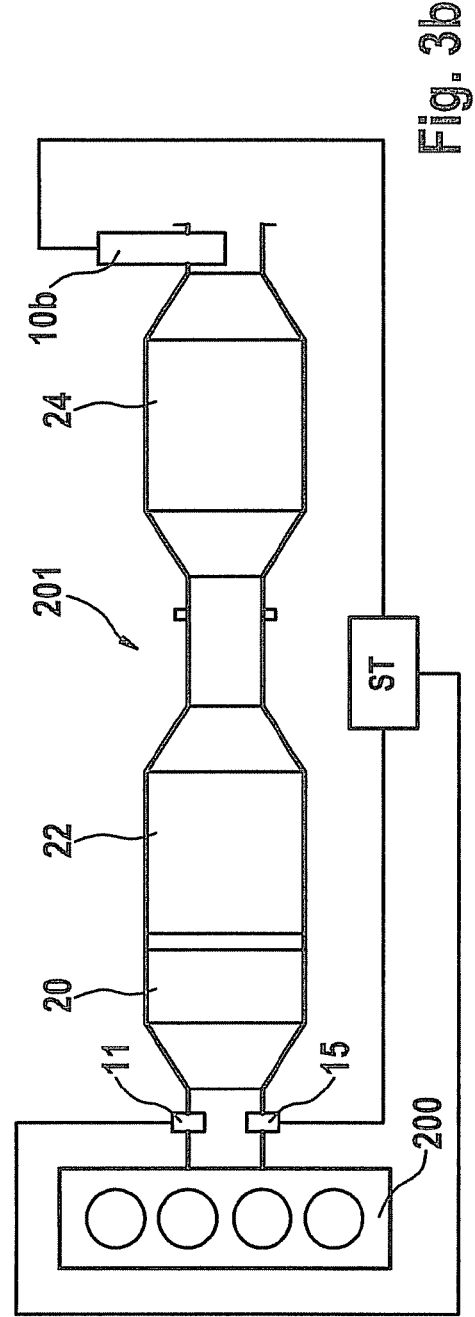

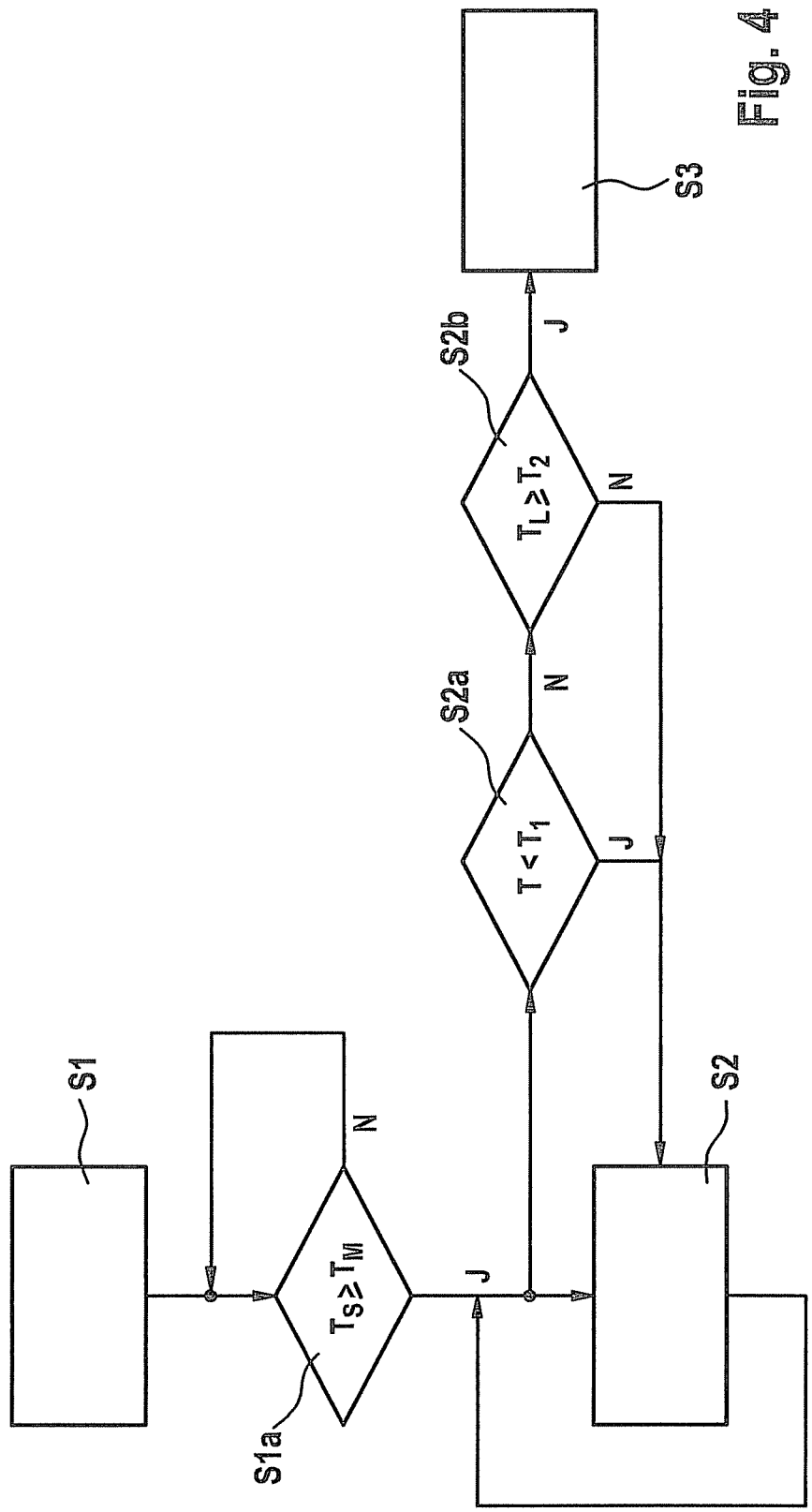

EXHAUST GAS SENSOR DEVICE, ENGINE CONTROL DEVICE AND METHOD

RELATED APPLICATION INFORMATION

The present application claims priority to and the benefit of German patent application no. 10 2009 027 374.3, which was filed in Germany on Jul. 1, 2009, the disclosure of which is incorporated herein by reference.

FIELD OF THE INVENTION

The present invention relates to an exhaust gas sensor device, an engine control device, and an engine control method.

BACKGROUND INFORMATION

Although applicable to any exhaust gas sensor devices, the exemplary embodiments and/or exemplary methods of the present invention and the problems on which it is based are explained from the standpoint of use in automobiles.

Due to ever more stringent exhaust gas legislation, the limiting values for gaseous pollutants are constantly being lowered. One main problem here is that most crude emissions (HC, CO, NOx, . . . ) are generated in the cold-start phase of the engine, i.e., as long as the engine is still relatively cold. To comply with the required low limiting values, early readiness of the exhaust gas sensors, in particular the lambda sensor, is urgently needed. This is counteracted by the high risk of water shock in the sensors (thermal shock of the lambda sensor) during the cold-start phase of the engine. After the last driving cycle, water collects in the exhaust gas line, which is deposited during a renewed start on the sensors not as water vapor but rather as water droplets due to the cold exhaust gas line. Thermal shock phenomena (thermomechanical loads and stresses) occur in the ceramic sensor element because a fully ready-to-use lambda sensor has an operating temperature above 680° C. As a countermeasure, lambda sensors are heated only slowly or not at all when starting the engine (for example, with a heating time of more than 30 s) or in increments with holding ramps. However, these delayed heating strategies are used at least long enough to reach the end of the dew point at the location of the lambda sensor. The end of the dew point is the point in time after which there is no longer any condenser water or the formation of condensate of water present in the exhaust gas is overcome. When the end of the dew point is reached at the location of the lambda sensor, the lambda sensor is heated as quickly as possible to the operating temperature (approximately 680° C.) because then there is only a reduced risk of water shock (thermal shock).

Until the end of the dew point in the exhaust gas and the operating temperature of the lambda sensor of more than 680° C. have been reached, the engine is in an unregulated state in which most of the crude emissions are generated. The required high use temperature of the lambda sensor is based on the sensor mechanism. Only at a temperature above 680° C. is the oxygen ion conductivity high enough in the yttrium-stabilized zirconium oxide (electrolyte) which supplies the sensor signal (current).

Presently there are not any known cost-relevant sensor concepts or measurement strategies whereby information about the oxygen concentration present in the exhaust gas could be obtainable during the cold-start phase.

Gas-sensitive field-effect transistors based on semiconductors (ChemFETs) are being used to an increasing extent in gas sensor systems. Semiconductor materials having a wide band gap, e.g., silicon carbide (SiC) and gallium nitride (GaN), are suitable for use in exhaust gas in particular. When the gas to be detected is applied, it usually results in a change in the current (channel current) flowing from the source electrode through the transistor to the drain electrode. Such a ChemFET based on silicon carbide as the hydrocarbon gas detection device is described in U.S. Pat. No. 5,698,771.

SUMMARY OF THE INVENTION

The exhaust gas sensor device according to the exemplary embodiments and/or exemplary methods of the present invention, the engine control device according to the exemplary embodiments and/or exemplary methods of the present invention, and the engine control method according to the exemplary embodiments and/or exemplary methods of the present invention have the advantage that oxygen is detectable at far lower temperatures before the end of the dew point than is the case with a lambda sensor, which may be above 100° C., because the ChemFET measuring principle is based on the adsorption of the respective gas species on the gas-sensitive electrode and thus may allow gas legislation for minimizing pollutant emissions at low temperatures.

ChemFETs are able to detect oxygen to a sufficient extent at sensor temperatures above 100° C. in particular. The exhaust gas temperature may be equal to or lower than the exhaust gas sensor temperature. Thus, within a few seconds (typically in the millisecond range, at any rate less than five seconds) the ChemFET exhaust gas sensor is ready for use immediately after starting the engine in the cold state. At these low sensor temperatures, thermal shock may be ruled out. An oxygen signal may therefore be used for engine gas legislation at a very early time. This ensures improved engine combustion and minimizes pollutant emissions. This may also yield a cost-optimized design of the exhaust gas after treatment systems such as a diesel oxidation catalyst, a particulate filter, a DeNOx system, an NSC catalyst, or an SCR catalyst. This in turn results in a smaller size, in less use of catalytically active components such as low-temperature storage materials for nitrogen oxides, NOx and the like and in the DeNOx system.

Since ChemFETs may be manufactured at a comparatively low cost in a small design size and in highly parallel semiconductor operations, multiple gas-sensitive field-effect transistors on a sensor substrate may be used. For example, there may be a redundant characteristic in the form of multiple oxygen-sensitive ChemFETs of the same design to increase the fault tolerance as well as the combination of gas-sensitive field-effect transistors having different sensitivities for detection of different gases in the exhaust gas ($NO_x$, HC, $NH_3$, $O_2$, . . . ) to control cross-sensitivities, for example, i.e., the response of one ChemFET to multiple different test gases.

The features characterized in the subclaims refer to advantageous refinements of and improvements on the object of the exemplary embodiments and/or exemplary methods of the present invention.

Exemplary embodiments of the present invention are shown in the drawings and are explained in greater detail in the following description.

BRIEF DESCRIPTION OF THE DRAWINGS

FIG. 3a shows a schematic diagram of an exhaust gas sensor device according to a third exemplary embodiment of the present invention.

FIG. 3b shows a schematic diagram of an exhaust gas sensor device according to a fourth exemplary embodiment of the present invention.

FIG. 4 shows a flow chart to illustrate an engine control method according to a fifth exemplary embodiment of the present invention.

DETAILED DESCRIPTION

Figures 1, 2:
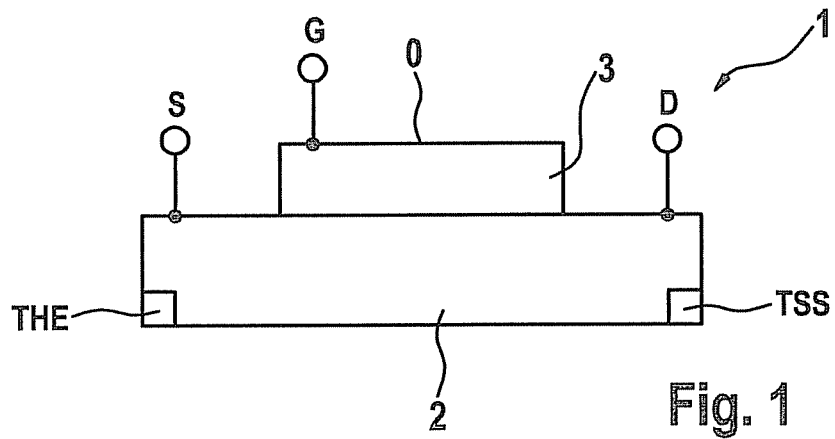
FIG. 1 shows a schematic diagram of an exhaust gas sensor device according to a first exemplary embodiment of the present invention.
FIG. 2 shows a schematic diagram of an exhaust gas sensor device according to a second exemplary embodiment of the present invention.

The same reference numerals in the figures denote the same elements or those having the same function. FIG. 1 shows a schematic diagram of an exhaust gas sensor device according to a first exemplary embodiment of the present invention.

FIG. 1 shows a ChemFET sensor 1 having a source electrode S and a drain electrode D connected to a substrate 2. A gas-adsorbing layer 3 is provided between source electrode S and drain electrode D on substrate 2, which may be a silicon carbide layer, which may additionally be coated with a catalytic material on its surface O, on which the gas species to be detected are adsorbed. A heating device THE, for example an electric resistance heater, is integrated into ChemFET sensor 1 for heating to an operating temperature of typically at least 100° C. A temperature detection device TSS, for example a meandering resistance wire or a temperature measurement section, is also integrated.

A varying potential is advantageously applied to gate electrode G during detection, as explained in detail in U.S. Pat. No. 5,698,771.

Surface O of layer 3 may be designed to be either oxygen sensitive or oxygen selective. The oxygen-sensitive electrode form is characterized in that it is made of platinum, a mixed metal or alloy containing platinum or any other oxygen-sensitive exhaust gas-robust material. According to the present exemplary embodiment, the oxygen content in the exhaust gas may be measured at between 0% and 21%. The oxygen electrode may have a (nano)porous structure but may also have a closed electrode structure.

At low oxygen concentrations (0 ppm-100 ppm) a sufficiently high sensitivity with a resulting precision in the range between ±20 ppm, in particular between ±10 ppm, may be achieved. Oxygen concentrations between 100 ppm and 1000 ppm are measured with a precision of ±100 ppm, in particular between ±50 ppm. Oxygen concentrations between 1000 ppm and 10,000 ppm are measured with a precision of ±1000 ppm, in particular between ±100 ppm. Oxygen concentrations between 10,000 ppm and 210,000 ppm are measured with a precision of ±50,000 ppm, in particular between ±1000 ppm.

ChemFET sensor 1 may be operated at any low temperature, at ambient temperature, if necessary. However, a reliable sensor signal is to be expected only above approximately 100° C. because only then is it possible to assume a water-free sensor electrode coverage, i.e., there is no longer any liquid water on surface O. ChemFET sensor 1 is then able to measure the oxygen content over any temperature range up to 600° C. This is appropriate in this form because the exhaust gas heats up with an increasing running time of the engine and the ambient temperature rises. The signal is compared with characteristic lines over the entire temperature range because the oxygen sensor signal is a function of temperature. The level of the ChemFET sensor signal is proportional to the oxygen concentration and is stored as a characteristic line for each temperature in the engine control unit. ChemFET sensor 1 is advantageously operated until full readiness of the lambda sensor has been established, i.e., at least during the first 30 seconds after a cold start or until exceeding the dew point at the location of the lambda sensor.

FIG. 2 shows a schematic diagram of an exhaust gas sensor device according to a second exemplary embodiment of the present invention.

ChemFET exhaust gas sensor device 1' shown in FIG. 2 has a plurality of ChemFET sensors 1a, 1b, 1c, 1d on a shared substrate 5 having various sensor functions. For example, ChemFET sensor 1a is sensitive to oxygen, ChemFET sensor 1b is sensitive to NOx, ChemFET sensor 1c is sensitive to CO, and ChemFET sensor 1d is sensitive to HC. Several ChemFET sensors 1a through 1d are advantageously operated using a multiplexer 50, which supplies an output signal OUT to an engine control unit. This reduces the required number of cables for operating such a ChemFET array 1'. The general design of sensors 1a through 1d corresponds to that of sensor 1 according to FIG. 1.

FIGS. 3a, b show a schematic diagram of engine control devices according to a third and a fourth exemplary embodiment of the present invention.

The exemplary embodiments in FIGS. 3a, b show an internal combustion engine 200 having an exhaust gas line 201. Exhaust gas line 201 has a diesel oxidation catalyst 20, a diesel particulate filter 22, and a DeNOx catalyst 24. This also shows a conventional lambda sensor 15 and a ChemFET sensor device 10a, 10b, as described in conjunction with FIGS. 1 and 2, for example. ChemFET sensor device 10a and 10b and lambda sensor 15 are connected to an engine control unit ST.

The general design of sensors 10a, 10b corresponds to that of sensor 1 according to FIG. 1. In addition, a temperature sensor 11 for detecting exhaust gas temperature T is connected to engine control unit ST. The temperature sensor in the exhaust gas line system installed nearest to the location of the lambda sensor may be used as temperature sensor 11.

In the exemplary embodiment according to FIG. 3a, ChemFET sensor device 10a is situated between diesel particulate filter 22 and DeNOx catalyst 24, while in the exemplary embodiment according to FIG. 3b, ChemFET sensor device 10b is situated downstream from DeNOx catalyst 24.

In the exemplary embodiment according to FIG. 3a, a ChemFET NOx sensor has an additional oxygen electrode for regulating DeNOx catalyst 24. In the exemplary embodiment according to FIG. 3b, an OBD NOx sensor based on ChemFET has an additional oxygen electrode. Sensor 10b according to FIG. 3b is situated downstream from DeNOx catalyst 24 and is used to monitor the function of the DeNOx catalyst. The placement at the end of exhaust gas line 201 is advantageous because the temperature burden on the ChemFET sensor is lower there than at other locations in the exhaust gas line.

FIG. 4 shows a flow chart to illustrate an engine control method according to a fifth exemplary embodiment of the present invention.

In the exemplary embodiment of the engine control method according to the present invention as illustrated in FIG. 4, the program sequence is initiated by a cold start in step S1. In step S1a, the ChemFET sensor is heated to minimum operating temperature $T_M$, for example, >100° C. on the maximum possible heating ramp immediately after a cold start. Heating device THE (e.g., an electric resistance heater) is used for heating to minimum operating temperature $T_M$. For temperature monitoring, temperature detection device TSS is integrated into the ChemFET sensor, which measures ChemFET sensor temperature $T_S$.

This step is performed until ChemFET sensor temperature $T_S$ is equal to or greater than minimum operating temperature $T_M$. If this is the case, then in step S2 the ChemFET sensor measures the oxygen content in the exhaust gas and the engine control is regulated on this basis. At the same time, step S2a detects whether exhaust gas temperature T is below temperature threshold value T1, which stands for the end of the dew point in the location of the lambda sensor (e.g., 100° C.). If that is the case, then in step S2 the engine is regulated on the basis of the oxygen content in the exhaust gas as detected by ChemFET sensor 10a or 10b. The program then runs through a loop of step S2a and step S2 until step S2a yields the result that temperature T in the exhaust gas line is greater than or equal to temperature T1 of 100° C., i.e., the end of the dew point has been reached at the location of lambda sensor 15. If this is the case, the program then branches off to step S2b and the temperature of lambda sensor 15 is heated on a maximum heating ramp up to its operating temperature T2, e.g., 680° C. If this is not yet the case, then in step S2 the engine is regulated on the basis of the oxygen content in the exhaust gas as detected by ChemFET sensor 10a and 10b. The program next runs through a loop of step S2a, step S2b, and step S2 until step S2b yields the result that lambda sensor temperature $T_L$ in the exhaust gas line is greater than or equal to operating temperature T2 of 680° C. of lambda sensor 15. If this is the case, the program branches off to step S3, according to which engine control unit ST performs the engine regulation based on the oxygen concentration in the exhaust gas as detected by lambda sensor 15.

Figure 5:
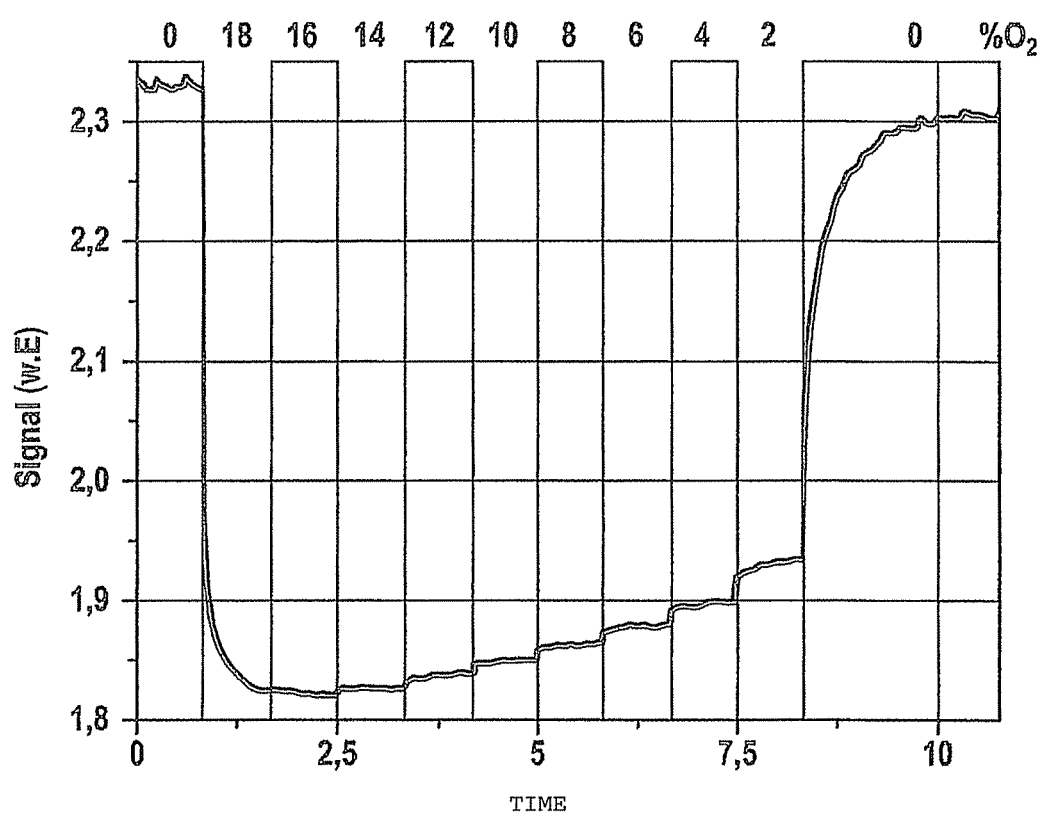
FIG. 5 shows a diagram of a ChemFET sensor signal as a function of the oxygen content in the exhaust gas and the period of time elapsed after a cold start.

FIG. 5 shows a diagram of a ChemFET sensor signal in arbitrary units as a function of the oxygen content and the time elapsed after a cold start, likewise shown in arbitrary units. FIG. 5 shows in particular an exemplary measurement of the oxygen content of 0% to 18% as a function of time. The abscissa shows the sensor signal of oxygen-sensitive ChemFET exhaust gas sensor 10a or 10b corresponding to the concentration of 0% to 18%.

Although the exemplary embodiments and/or exemplary methods of the present invention was described above on the basis of the exemplary embodiments, it is not limited thereto but instead may be modified in a variety of ways.

Although applications in the automotive field were discussed in the exemplary embodiments described above, the exemplary embodiments and/or exemplary methods of the present invention are not limited to these applications but instead may be used for any internal combustion engines. Other or additional engine parameters may also be used for switching the engine control unit from one oxygen sensor to the other. Furthermore, the heating device and the temperature detection device need not be integrated but instead may be formed by separate components.

What is claimed is:

1. An exhaust gas sensor device for detecting a concentration of at least one exhaust gas component in the exhaust gas line of an internal combustion engine, comprising:
    a lambda sensor for detecting the oxygen content of the exhaust gas;
    at least one gas-sensitive field-effect transistor for detecting an oxygen content of the exhaust gas; and
    a control unit configured to perform an engine control based on the oxygen content of the exhaust gas detected by each field-effect transistor when an operating temperature of the lambda sensor has not been reached, and based on the oxygen content of the exhaust gas detected by the lambda sensor when the lambda sensor has reached the operating temperature;
    wherein the at least one gas-sensitive field effect transistor is located in an exhaust gas line, downstream of the lambda sensor and downstream of a DeNOx catalyst, and wherein the lambda sensor is located upstream of the DeNOx catalyst.

2. The exhaust gas sensor device of claim 1, wherein the at least one gas-sensitive field-effect transistor includes a plurality of gas-sensitive field-effect transistors provided on a single carrier.

3. The exhaust gas sensor device of claim 2, wherein all of the plurality of gas-sensitive field-effect transistors are provided for detecting the oxygen content of the exhaust gas.

4. The exhaust gas sensor device of claim 2, wherein at least one of the plurality of gas-sensitive field-effect transistors is provided for detecting a concentration of an exhaust gas component different from the oxygen content.

5. The exhaust gas sensor device of claim 1, further comprising:
    at least one of an integrated temperature detection device and an integrated heating device.

6. An engine control device, comprising:
    a first exhaust gas sensor device configured to detect an oxygen content of an exhaust gas using a lambda sensor; and
    a second exhaust gas sensor device, wherein the second exhaust gas sensor device has at least one gas-sensitive field-effect transistor to detect the oxygen content of the exhaust gas; and
    a control unit configured to perform an engine control, in a first engine parameter range, based on the oxygen content of the exhaust gas detected by the first exhaust gas sensor device, and to perform an engine control, in a second engine parameter range, based on the oxygen content of the exhaust gas detected by the second exhaust gas sensor device;
    wherein the at least one gas-sensitive field effect transistor is located in an exhaust gas line, downstream of the lambda sensor and downstream of a DeNOx catalyst, and wherein the lambda sensor is located upstream of the DeNOx catalyst.

7. The engine control device of claim 6, wherein the first engine parameter range and the second engine parameter range are a first exhaust gas temperature range and a second exhaust gas temperature range.

8. The engine control of claim 7, wherein the first exhaust gas temperature range is a range above a dew point temperature at a location of the lambda sensor, and wherein the second exhaust gas temperature range is a range below a dew point temperature at the location of the lambda sensor.

9. The engine control device of claim 7, further comprising:
    a temperature sensor that outputs an indication of a current exhaust gas temperature to the control unit.

10. The engine control device of claim 6, wherein each gas-sensitive field-effect transistor includes a heating device that heats the gas-sensitive field effect transistor to a respective operating temperature, which is below an operating temperature of the lambda sensor.

11. The engine control device of claim 10, wherein the control unit waits until each gas-sensitive field effect transistor has reached its respective operating temperature before performing the engine control based on the oxygen content of the exhaust gas detected by the second exhaust gas sensor device.

12. An engine control method, the method comprising:
- detecting an engine parameter of an internal combustion engine;
- ascertaining whether a detected engine parameter is in a predefined first engine parameter range or a second engine parameter range; and
- performing an engine control based on an oxygen content of an exhaust gas detected by a first exhaust gas sensor device configured to detect the oxygen content of the exhaust gas using a lambda sensor, when the engine parameter is in the first engine parameter range;
- performing an engine control based the oxygen content of the exhaust gas detected by a second exhaust gas sensor device, the second exhaust gas sensor device having at least one gas-sensitive field-effect transistor for detecting the oxygen content of the exhaust gas when the engine parameter is in the second engine parameter range;
- placing the at least one gas-sensitive field effect transistor in an exhaust gas line, downstream of the lambda sensor and downstream of a DeNOx catalyst; and
- placing the lambda sensor upstream of the DeNOx catalyst.

13. The engine control method of claim 12, wherein the first engine parameter range and the second engine parameter range are a first exhaust gas temperature range and a second exhaust gas temperature range.

14. The engine control method of claim 13, wherein the first exhaust gas temperature range is a range which is above a dew point temperature at a location of the lambda sensor, and wherein the second exhaust gas temperature range is a range which is below a dew point temperature at the location of the lambda sensor.

15. The engine control method of claim 13, further comprising:
- using a temperature sensor to determine a current exhaust gas temperature.

16. The engine control method of claim 12, further comprising:
- heating each gas-sensitive field-effect transistor using a respective heating device to a respective operating temperature, which is below an operating temperature of the lambda sensor.

17. The engine control method of claim 16, further comprising:
- waiting until each gas-sensitive field effect transistor has reached its respective operating temperature before performing the engine control based on the oxygen content of the exhaust gas detected by the second exhaust gas sensor device.

* * * * *